US006733728B1

(12) United States Patent
Mimura et al.

(10) Patent No.: US 6,733,728 B1
(45) Date of Patent: *May 11, 2004

(54) ANALYZER SYSTEM HAVING SAMPLE RACK TRANSFER LINE

(75) Inventors: Tomonori Mimura, Tomobe-machi (JP); Hiroshi Mitsumaki, Mito (JP); Tadashi Ohishi, Ibaraki-machi (JP); Taku Sakazume, Hitachinaka (JP)

(73) Assignee: Hitachi, Ltd., Tokyo (JP)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 2 days.

This patent is subject to a terminal disclaimer.

(21) Appl. No.: 09/220,371

(22) Filed: Dec. 24, 1998

Related U.S. Application Data

(63) Continuation of application No. 08/813,872, filed on Mar. 7, 1997, now Pat. No. 5,902,549.

(30) Foreign Application Priority Data

Mar. 11, 1996 (JP) ................................................ 8-52870

(51) Int. Cl.[7] .............................................. G01N 35/00
(52) U.S. Cl. ........................................ 422/65; 422/67
(58) Field of Search .................... 422/65, 67; 436/43, 436/47, 48, 49, 50

(56) References Cited

U.S. PATENT DOCUMENTS

| 3,644,095 A | | 2/1972 | Netherier et al. |
| 4,451,433 A | | 5/1984 | Yamashita et al. |
| 5,087,423 A | | 2/1992 | Ishibashi |
| 5,207,986 A | * | 5/1993 | Kadota et al. ................. 422/65 |
| 5,260,868 A | | 11/1993 | Gupta et al. |
| 5,348,705 A | | 9/1994 | Koreyasu et al. |
| 5,357,095 A | | 10/1994 | Weyrauch et al. |
| 5,380,488 A | * | 1/1995 | Wakatake ...................... 422/65 |
| 5,428,470 A | * | 6/1995 | Labriola, II .................. 359/119 |
| 5,434,083 A | | 7/1995 | Mitsumaki et al. |
| 5,902,549 A | * | 5/1999 | Mimura et al. ................ 422/63 |
| 5,972,295 A | * | 10/1999 | Hanawa et al. ................ 422/63 |
| 5,985,215 A | * | 11/1999 | Sakazume et al. ............. 422/67 |
| 6,019,945 A | * | 2/2000 | Ohishi et al. .................. 422/63 |
| 6,080,364 A | * | 6/2000 | Mimura et al. ................ 422/63 |
| 6,290,907 B1 | * | 9/2001 | Takahashi et al. ........... 422/100 |
| 2002/0016683 A1 | * | 2/2002 | Shiba et al. ................... 702/22 |

FOREIGN PATENT DOCUMENTS

| EP | 558 212 A2 | 1/1993 |
| JP | 58-123460 | 7/1983 |
| JP | 63-271164 | 11/1988 |
| JP | 63271164 | 11/1988 |
| JP | 2-25755 | 1/1990 |
| JP | 02025755 | 1/1990 |
| JP | 02064463 | 3/1990 |
| JP | 2-306165 | 12/1990 |
| JP | 3-99269 | 4/1991 |
| JP | 3-180763 | 8/1991 |
| JP | 7-92171 | 4/1995 |

OTHER PUBLICATIONS

T. Ikeda, Total Clinical Laboratory Testing System for Laboratory Automation, 8297 Hitachi Review, Sep. (1992), No. 4.

* cited by examiner

Primary Examiner—Jill Warden
(74) Attorney, Agent, or Firm—Mattingly, Stanger & Malur, P.C.

(57) ABSTRACT

A plurality of analyzer units for serum, a plurality of analyzer units for blood plasma and a plurality of analyzer units are arranged along a main transfer line for transferring a sample rack from a rack delivery portion to a rack returning portion. A reagent bottle for inspecting liver function is contained in each of reagent delivery mechanisms of two analyzer units among the plurality of analyzer units for serum. When reagent for inspecting liver function in one of the two analyzer units is to be short, analysis for liver function analysis item to samples can be continued by transferring a sample rack from the rack delivery portion to the other analyzer unit.

2 Claims, 4 Drawing Sheets

ANALYZER SYSTEM HAVING SAMPLE RACK TRANSFER LINE

This application is a continuation of application Ser. No. 08/813,872 filed Mar. 7, 1997 now U.S. Pat. No. 5,902,549.

BACKGROUND OF THE INVENTION

The present invention relates to an analyzer system, and particularly to an analyzer system suitable for transferring a sample rack to a plurality of analyzer units though a transfer line, and analyzing and processing designated analysis items for a plurality of samples.

A multiple-sample analyzer system is known, in which a sample rack containing body fluid samples such as blood and urine is transferred to a plurality of analyzer units through a transfer line in order to inspect and analyze the body fluid samples.

As for the prior art, an automated analyzer system is disclosed in Japanese Patent Application Laid-Open No.62-271164. In the automated analyzer system, two or three kinds of analyzer units are arranged along a circulating transfer line composed of a belt conveyer. A transferred sample rack is identified with a bar code reader, and stopped in front of a designated analyzer unit to pipette a sample fluid into the analyzer unit. After that, the sample rack is transferred to the next analyzer unit to pipette the sample into the next analyzer unit, and finally the sample rack is returned to a stock yard.

Another analyzer system is disclosed in Japanese Patent Application Laid-Open No.2-25755. The analyzer system comprises a plurality of reaction units having different analysis functions arranged along a main transfer line, and a by-pass line for accepting a sample rack from the transfer line to a sampling position of the individual reaction unit to pipette the sample from the by-pass line to the reaction unit. In this analyzer system, a sample container containing a sample has a bar code label indicating the ID (identification) information, and a sample rack containing a plurality of sample containers also has a bar code label. The ID information of the sample on the sample rack transferred on the main transfer line is read out and a reaction unit corresponding to the sample is determined. In case that the designated reaction unit is occupied for sampling another sample, the sample rack is transferred back again to the upper stream of the main transfer line through the return transfer line. This cyclic operation is repeated until the designated reaction unit becomes empty.

In Japanese Patent Application Laid-Open No.63-271164, the biochemical analysis of the sample by an analyzer unit is implicated, but there is no definite description on how to deal with the analysis item and the reagent to be used. In the analyzer system disclosed in Japanese Patent Application Laid-Open No. 2-25755, as the system is configured so that the individual analysis units may have their own distinctive functions, the individual analysis item is processed by its own specific analysis unit. Therefore, a sample having an analysis item requested by a large number of samples has to wait for completion of analyzing the preceding samples for a longer time than the samples with another analysis item requested by a small number of samples, and consequently, it takes a long time for those samples to obtain the analysis data.

SUMMARY OF THE INVENTION

An object of the present invention is to provide a multiple sample analyzer system which enables an efficient analysis operation even for the analysis item which is requested by a large number of samples, and enables an automated analysis operation without interrupting the analysis operation for the analysis item for which the reagent fluid is short while the analyzer unit is operated.

The present invention is applied to an analyzer system comprising a transfer line for transferring a sample rack from a rack providing portion to a rack storage portion, and a plurality of analyzer units each having a reaction unit, a sample pipetting unit for pipetting a sample on the sample rack into the reaction unit, and a reagent supply unit for supplying a reagent corresponding to an analysis item to the reaction unit, the plurality of analyzer units being arranged along the transfer line, and a large number of samples being inspected and analyzed using the plurality of analyzer units. In the present invention, an analysis-item corresponding reagent used for the same kind of designated analysis item is allocated to a designated analyzer unit and another analyzer unit of the plurality of analyzer units, respectively, and the above designated analysis item is processed by the designated analyzer unit. A control unit judges whether the amount of the above described analysis-item corresponding reagent is short or not in accompanying the consumption of this analysis-item corresponding reagent in the designated analyzer unit. In case that the amount of the analysis-item corresponding reagent is short, a sample rack having a sample specified to be analyzed with the designated analysis item is transferred to the another analyzer unit through the transfer line to analyze the designated analysis item for the sample using the another analyzer unit.

In a preferred embodiment of the present invention, the designated analyzer unit is determined automatically by the control unit, or the priority order for the usage of the analyzer unit is determined by an operator through the operating unit. In case of specifying the designated unit automatically, based on the read-out result of the identification information labeled on the sample rack or the sample container, the control unit judges which analyzer unit can process the specified analysis item when the sample rack is transferred by the transfer line, and the sample rack containing the sample for which the above described designated analysis item to be processed is transferred to the analyzer unit selected based on the above described judgment result through the transfer line. In this case, an analyzer unit which contains the least number of samples waiting for the inspection operation is selected by the control unit out from the plurality of analyzer units which enable the analysis operation for the specified analysis item.

In another preferred embodiment of the present invention, as for the above described analysis-item specific reagent contained in the specified analyzer unit, the control unit judges whether the number of remaining possible inspection operations decreasing along with the repetitive pipetting operations reaches a designated value, and based on the judged result, the control unit interrupts the analysis operation function for the designated analysis item in the specified analyzer unit and dispatches the analysis operation function for the designated analysis item to another analyzer unit. Before the analysis operation of the sample, the specified analyzer unit and the another analyzer unit calibrate their individual measurement light beams, and the calibration results for the measurement light beams, each corresponding to the individual analyzer unit, are stored in a memory unit. Finally the calibration result reflecting the property of the individual reagent bottle is reference for correcting the measurement value for the individual analyzer unit.

Further, a multi-sample analyzer system of the present invention has a function that the control unit judges the classification of the sample loaded in the sample rack, based on the read-out result of the identification information labeled on the sample rack or the sample container when the sample rack is transferred by the main transfer line, and that the sample rack with its analysis operation completed is made to be transferred to the analyzer unit in which the analysis condition is defined for the sample. In addition, the multiple sample analyzer system of the present invention has a means for directing the start-up and shutdown operations for each of plural analyzer units, and the control unit has a function for carrying the sample rack through the transfer line to the analyzer unit excluding the analyzer unit with its operation being suspended.

DESCRIPTION OF THE PREFERRED EMBODIMENT

Figure 1:
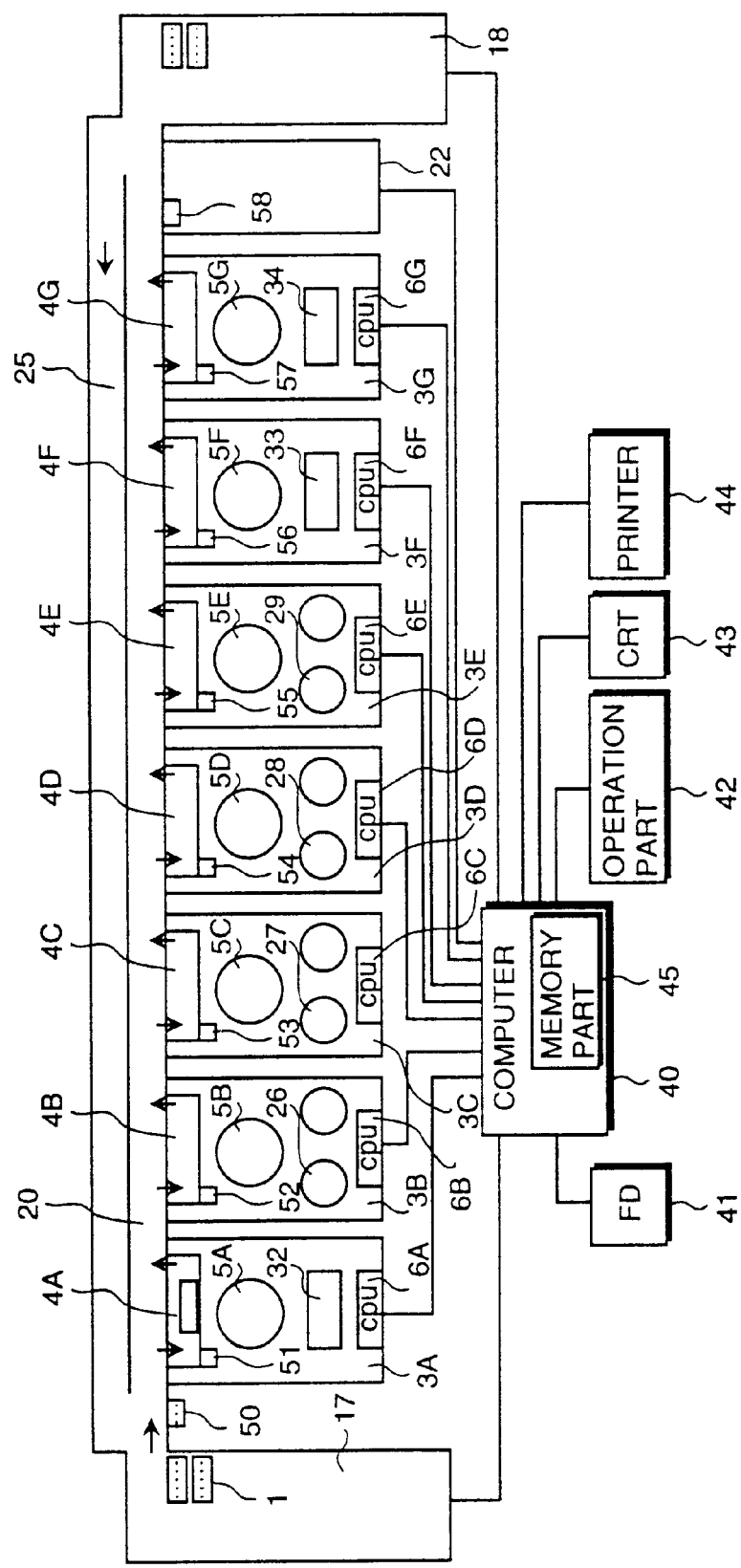
FIG. 1 is a schematic view showing the construction of an embodiment of an analyzer system to which the present invention is applied.
Figure 2:
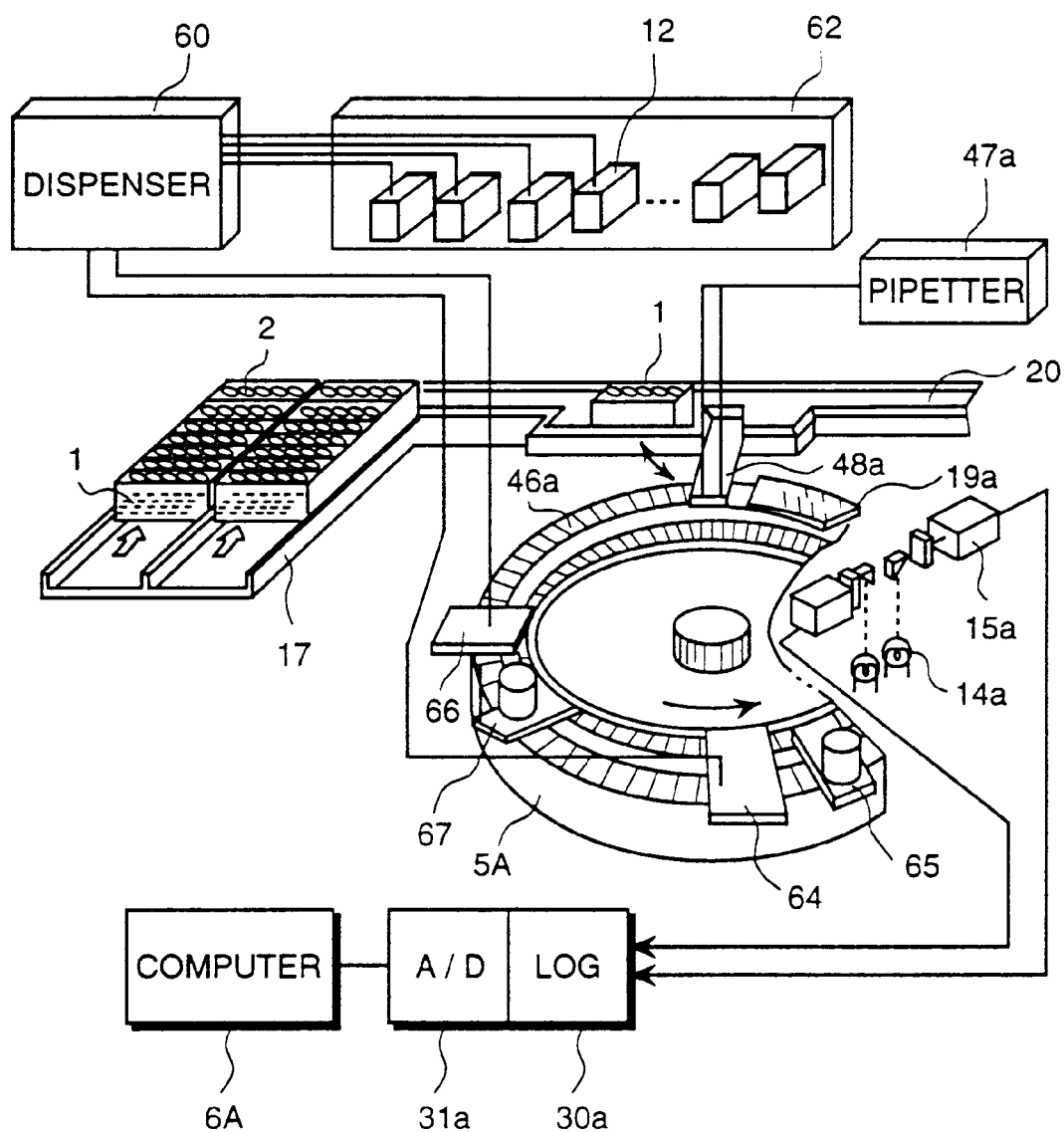
FIG. 2 is a view explaining an example of a dispenser-based analyzing unit in the embodiment shown in FIG. 1.

Preferred embodiments of the present invention will be described below, referring to FIG. 1 to FIG. 4. FIG. 1 shows a schematic construction of the multi-sample analyzer system enabling to analyze samples such as blood serum, blood plasma and urine. In the analyzer system shown in FIG. 1, an analyzer unit supplying samples in a dispenser method as shown in FIG. 2 and an analyzer unit supplying samples in a pipette method are involved. The analyzer units 3A, 3F and 3G in FIG. 1 are dispenser-method based analyzer units, each having fixed analysis channels in which a plurality of sample injection nozzles are assigned to specific samples individually. The analyzer units 3B, 3C, 3D and 3E having an analysis channel not fixed but accessed randomly are pipette-method based analyzer units in which a single reagent pipetting nozzle supplies a designated reagent corresponding to the individual analysis items in a controlled sequence.

In the analyzer units 3A, 3B and 3C shown in FIG. 1, the analysis conditions are so defined as to perform the analysis procedures for serum samples; the analysis conditions in the analyzer units 3D and 3E are so defined as to perform the analysis procedures for blood plasma samples; and the analysis conditions in the analyzer units 3F and 3G are so defined as to perform the analysis procedures for urine samples. The analyzer units 3A to 3G have sampling lines 4A to 4G used as transferring routes which have a function for positioning the sample rack 1 transferred from the main transfer line 20 in the sampling position and next returning the sample rack 1 back to the main transfer line 20; identification information reading unit 51 to 57 installed corresponding to the individual sampling line for reading out the identification information of the sample rack 1 or the identification information of the individual sample container contained in the individual sample rack 1; reaction parts 5A to 5G for measuring optically the reaction processes defined by the individual analysis item for the specified sample and reagent undergone in the reaction vessel; and a reagent delivery mechanism. Among the plural reagent delivery mechanisms of the individual analyzer unit, the reagent delivery mechanisms 26, 27, 28 and 29 are based on the pipette method, and the reagent delivery mechanisms 32, 33 and 34 are based on the dispenser method.

The rack providing part 17 has an area which can contain plural sample racks 1 and a carry out mechanism for carrying out a sample rack one by one to the main transfer line 20. The rack storage portion 18 has an area which can reserve plural sample racks 1 containing samples processed for designated analysis operations in the individual analyzer unit, and has a line-up mechanism for lining up sample racks in a row. The temporary storage part 22 stores the sample racks 1 which contain samples picked up by the analyzer unit for examination until the examination result is put out, and, if the re-examination is required for the designated sample, the corresponding sample rack 1 is returned to the main transfer line 20 by the re-examination rack transfer line 25; if the re-examination is not required, the designated sample rack is moved forward to the rack storage portion 18.

The control unit has a central control computer 40, analyzer unit computers 6A to 6G, and a floppy disk memory 41. The analyzer unit computers 6A to 6G process the output signals from the individual analyzer unit. The central control computer 40 connected to those individual analyzer unit computers 6A to 6G controls the operation of the individual analysis units, the rack transfer system and the related sub-parts in the analyzer system as well as performs numerical calculations and control actions necessary for designated information processing. Function assignment to the computers is not limited to the above example, but can be modified in response to various requirements on the system configuration, even including such a case that all the control functions conventionally assigned to the distributed analyzer unit computers can be integrated onto the central control computer 40 and the analyzer unit computers can be retired. The central control computer 40 includes a memory unit 45, to which are connected the operation unit 42 used for data input, the CRT 43 for displaying information visually, and the printer 44 for outputting the measurement and examination results.

The sample rack 1 is, for example shown in FIG. 2, composed of a vessel container shaped in a box in which a plurality of sample containers 2, for example, five sample containers, are contained in a single vessel container. The shape of the vessel container is not limited to a box but various shapes can be used. On the outer wall of the sample rack 1, an information identification medium for representing the rack identification information is mounted. Bar code labels and magnetic recording media are used as information identification media. A bar code labeled on the sample rack 1 has an information related to the rack identification number and sample classifications. A bar code labeled on the sample container 2 has an information related to the individual sample, for example, registration identification number, registration date, patient name, patient identification number, sample classification and designated analysis items.

The identification information read-out unit 50 shown in FIG. 1 reads out the data from the identification information (bar code) labeled on the sample rack 1 or the sample container 2 before carrying by the main transfer line 20, and supplies the read-out data to the computer 40. In addition, the identification information read-out unit 58 installed in the temporary storage part 22 reads out the bar code labeled on the sample rack or the sample container when the sample rack 1 enters the temporary storage part 22 as well as leaves the temporary storage part 22, and transfers the read-out data to the central control computer 40.

The sample identification information is labeled with bar codes on the outer wall of the reagent bottles 12, 12A and 12B used for the individual analysis items to be contained in the reagent delivery mechanisms in the analyzer units 3A to 3G. The reagent identification information includes the reagent manufacturing lot number, the size of the reagent bottle, the available amount of reagent fluid for analysis, the valid date of the reagent for analysis, the sequential distinctive number assigned to the individual bottle, the analysis item code and so on. The sample identification information is read out by the bar code read-out unit, and assigned to any of the specific analyzer unit 3A to 3G. The set position of the reagent bottle in the reagent delivery mechanism, the maximum number of analysis operations calculated by the available amount of the reagent fluid and the amount of the reagent fluid used at a single analysis operation, the specification of the analysis item, and the identification number of the analyzer units in which the reagent is transferred are stored in the memory unit 45.

The main transfer line 20 has a carry belt on which the sample rack 1 is mounted and a belt drive motor, and is controlled by the control part so as to transport continuously the sample rack in a designated position. The individual sampling lines 4A to 4G can move intermittently the carry belt so as to make the rack stop at the rack lead-in position, the fluid injection position and the rack send-out position. The sample rack 1 transferred by the main transfer line 20 is moved along the line defined by the array of the analyzer units, made to stop in front of the analyzer unit specified by the control unit, and moved immediately to the rack lead-in position on the sampling line by the rack loading mechanism, not shown in FIG. 1. The sample rack 1 with its sampling operation completed at the sampling position is transferred from the rack send-out position on the sampling line to the main transfer line 20 by the rack loading mechanism. As for the rack loading mechanism, a movable robot having a rack grip arm and a mechanism having a push lever for pushing the sample rack from the front side to the back side on the main transfer line and the sampling line.

An example of the structure of the dispenser-method based analyzer unit is described by referring to FIG. 2. The reaction part 5A of the analyzer unit 3A has two rows of transparent reaction vessels 46a, each series arranged on a concentric circle, and each series has a multi-spectral photometer 15a for spectroscopic operation on the light emitted from the light source 14a and passed through the reaction vessel 46A. In the neighboring area of the reaction part 5A, arranged are the sample pipetting mechanism 48a having a pipette nozzle connected to the sample pipetter pump 47a, the first reagent nozzle-group support part 64 and the second reagent nozzle-group support part 66 connected to the reagent dispenser pump 60, the first stirring mechanism 65 and the second stirring mechanism 67, and the reaction vessel rinse mechanism 19a. The reagent bottles 12 for the first reagent and the second reagent (only for the necessary analysis items) for the plurality of analysis items are arranged in the reagent cooler 62 and their reagent temperature is maintained in a designated value. The reagent fluid the individual reagent bottle 12 is supplied to the corresponding reagent ejection nozzle on the array of reaction vessels by the reagent dispenser pump 60. In this embodiment, the dispenser-method based reagent delivery mechanism 32 in the analyzer unit 3A shown in FIG. 1 includes the reagent dispenser pump 60 shown in FIG. 2, the reagent cooler 62 containing plural reagent bottles 12, the first reagent nozzle-group support part 64 and the second reagent nozzle-group support part 66.

The individual sample rack 1 supplied from the rack providing part 17 is transferred by the main transfer line 20, and in case that the analysis process by the analyzer unit 3A is necessary, the sample rack 1 so transferred is loaded on the sampling line 4A of the analyzer unit 3A. When the sample on the sample rack 1 is positioned on the pipetting position, a designated amount of the sample fluid is extracted from the sample rack and pipetted into the reaction vessel 46a by the pipette nozzle of the sample pipetting mechanism 48a. The specified reagent corresponding to the designated analysis item is injected into the reaction vessel located on a designated position in the series of reaction vessels, and biochemical reaction occurs in it. After a designated period of time, the optical characteristic of the reactive fluid contained in the reaction vessel 46a is measured by the multi-spectral photometer 15a. The output signal from the multi-spectral photometer 15a is processed by the logarithmic converter 30a and the A/D converter 31a both controlled by the analysis computer 6A, and is transferred to the central control computer 40. The dispenser-method based analysis systems 3F and 3G have the similar structure to the structure of the analyzer unit 3A.

Figure 3:
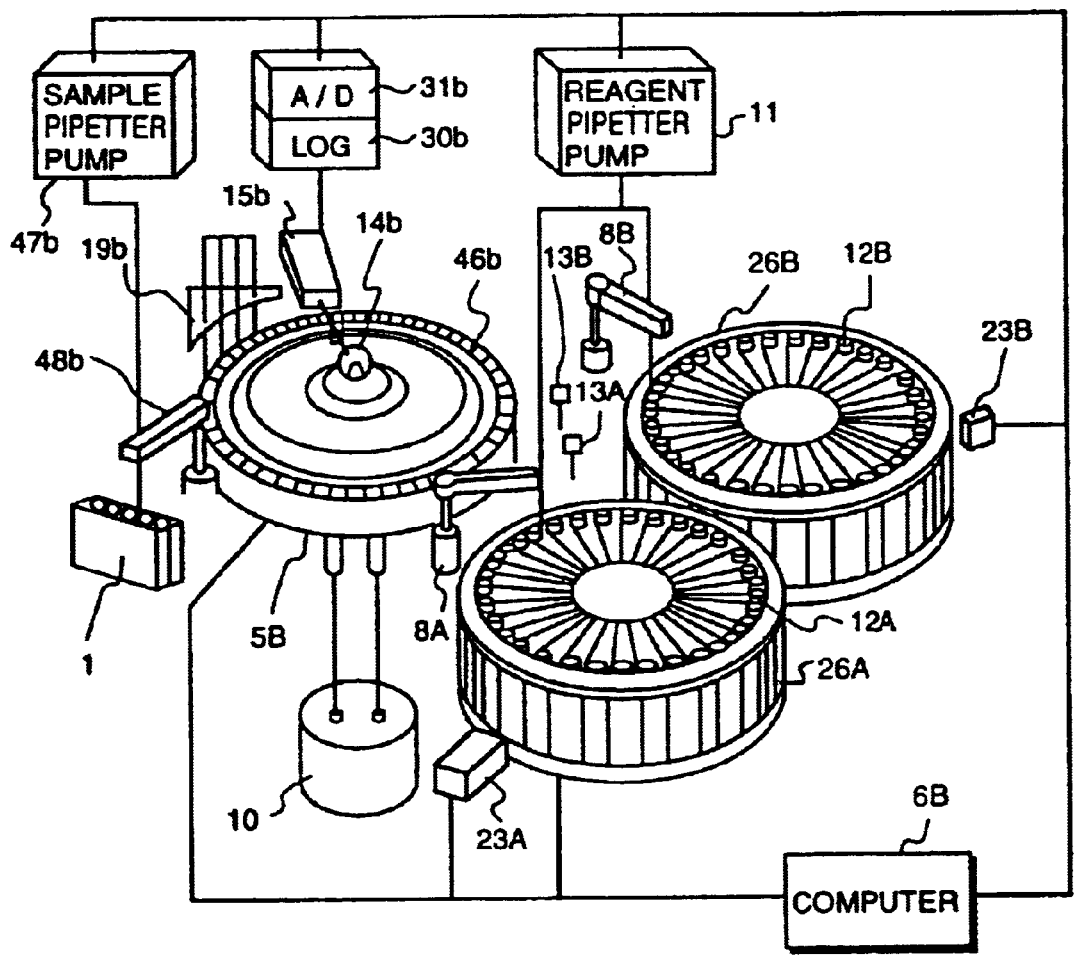
FIG. 3 is a view explaining an example of a pipette-based analyzing unit in the embodiment shown in FIG. 1.

Next, an example of the pipetter-method based analyzer unit is described by referring to FIG. 3. A biochemical reaction for the sample and the reagent related to the designated analysis item is undergone in the reaction vessel arranged in the reaction part 5B in the analyzer unit 3B. The sample rack 1 moved from the main transfer line 20 to the sampling line 4B (FIG. 1) is located at the pipetting position, where a designated amount of the specified sample in the sample rack 1 is picked up and pipetted into the reaction vessel 46b by the pipette nozzle of the sample pipetting mechanism 48b. The sample pipetting mechanism 48b has a sample pipetter pump 47b. The temperature in the reaction part 5B is maintained at a constant value, for example, 37° C.

The pipetter-method based reagent delivery mechanism 26 of the analyzer unit shown in FIG. 3 has a couple of reagent disks 26A and 26B used for the first reagent and the second reagent, respectively. The bar codes representing the reagent identification information are labeled on the outer walls of the reagent bottles 12A and 12B containing reagents prepared for plural analysis items. When the reagent bottles 12A and 12B are loaded on the reagent disks 26A and 26B, the reagent identification information recorded on the bar codes is read out by the bar code read-out units 23A and 23B, and the read-out information including the set position of the reagent bottles on the reagent disks, the designated analysis items, and the analyzer unit number on which the reagent bottles are mounted is stored on the memory unit 45. The reagent pipetting mechanisms 8A and 8B have reagent pipette pumps 11 connected to the pipette nozzles which can rotate freely and move up and down.

The row of reaction vessels 46b into which the samples are pipetted are moved in a rotational direction, a designated amount of reagent is picked up by the reagent pipetting mechanism 8A from the reagent bottle 12A positioned at the designated pipetting position corresponding to the specified analysis item, and the first reagent is injected into the reaction bottle 46b positioned at the reagent injection position. After the reaction fluid including the sample fluid and the injected reagent fluid is stirred by the stirring mechanism 13A at the stirring position, the series of reaction vessels are moved in a rotational direction until the reaction vessel 46b reaches the first reagent injection position, where the reagent pipetting mechanism 8B samples out the reagent from the reagent bottle 12A positioned at the reagent pipetting position corresponding to the specified analysis item, and injects the reagent into the reaction vessel. Next, the reaction fluid contained in the reaction vessel is stirred by the stirring mechanism 13B. Thereafter, the light beam from the light source 14b penetrates through the reaction vessel 46B in accordance with the rotational movement of the series of reaction vessels, and the light beam penetrated through the reaction fluid contained in the reaction vessel 46b is detected by the multi-spectral photometer 15b. The spectral signals corresponding to the designated analysis item are processed by the logarithmic converter 30b and the A/D converter 31b, both controlled by the analyzer unit computer 6B, and the processed digital signal is forwarded to the central control computer 40. The reaction vessel 46b completed with designated analysis processes is rinsed by the rinse mechanism 19b and recycled. The analyzer unit 3C, 3D and 3E have a similar structure to the analyzer unit 3B.

The operation of the analyzer unit shown in FIG. 1 will be described below.

Before the sample rack 1 is set on the rack providing part 17, the analysis items as well as the sample identification number for the individual samples specified by the applicant for analysis are registered into the central control computer 40 by the operation console 42 before analysis operation. The analysis condition information for the individual analysis item is stored on the floppy disk memory 41. The analysis item code in the analysis condition information comprises 5-digit numerals. The analysis condition parameter to be used commonly in the plurality of analyzer units for the identical analysis item includes the wavelength of the light used for measurement by the photometer, the amount of sample to be pipetted, the calibration method of calibration curves, the reference fluid concentration, the number of reference fluid samples, threshold parameters for detecting abnormal analysis conditions and so on. The parameters so stored as to be corresponding to the individual reagent bottle among the analysis condition parameters include necessary number of reagents from the first reagent to the fourth reagent, the code of the reagent bottle coded in a 5-digit number, the amount of pipetted reagent, the available testing number per single reagent bottle and so on. The conditions of the individual analyzer unit are defined so that the analyzer units 3A, 3B and 3C can accept the serum samples, the analyzer units 3D and 3E can accept the blood plasma samples, and that the analyzer units 3F and 3G can accept the urine samples. The analyzer unit identification numbers and the acceptable sample specifications are registered in the central control computer.

Accompanying the loading operation of the reagent bottle into the reagent delivery mechanism of the individual analyzer units 3A to 3G, the reagent identification information of the individual reagent bottles is registered into the central control computer 40 so as to correspond to the designated analyzer unit. In this case, the reagent used for an identical analysis item is loaded onto a plurality of analyzer units categorized in a group of analyzer units handling an identical sample class. For example, the analyzer units 3A, 3B and 3C are categorized in a group of analyzer units for the serum samples. In this case, the reagent bottles used for GOT and GPT generally as frequently requested analysis items and the reagent bottles used for calcium, UA and BUN as emergency analysis items are loaded in the reagent delivery mechanism 32 of the analyzer unit 3A. Also, the reagent bottle used for GOT and GPT as the liver function inspection analysis item and used for the analysis items not so often requested are loaded in the reagent delivery mechanism 26 of the analyzer unit 3B. The reagent bottle used for calcium, UA and BUN as emergency analysis items and for the inspection analysis items not so often requested are loaded in the reagent delivery mechanism 27 of the analyzer unit 3C. The reagent for the specific analysis item that is to be multiply loaded on the plural analyzer unit is determined by the analysis operator in considering the operational condition of the individual inspection facility.

Accompanying the loading operation of the reagent bottles 12, 12A and 12B on the individual reagent delivery mechanisms, the reagent identification information labeled on the individual reagent bottle is read out. The information already registered as the analysis condition parameters is searched with the reagent bottle code as the search key, and the analysis items corresponding to the individual reagent bottle, the size of the bottle, the maximum number of inspection operations enabled with the reagent content in the single reagent bottle, the set position of the reagent bottle and are made to be related to one another and registered in the central control computer 40. At the same time, the maximum number of inspection analysis operations is estimated with the number of all the reagent bottles for the identical analysis item in the plurality of analyzer units enabling the identical analysis item is also registered in the central control computer and displayed on a CRT 43 if necessary.

After loading the reagent bottles necessary for the designated analysis items at the individual analyzer unit, the calibration operation of the calibration curve is performed for all the analyzable analysis items in each of the analyzer units is performed prior to the analysis operation for the sample is performed. Because the calibration value of the calibration curve is subject to the individual reagent bottle loaded in the designated analyzer unit, the calibration results obtained by the individual analyzer units for the individual analysis items are registered in the memory unit 45 of the central control computer 40. Those calibration results are used for the density calculation when the designated analysis item is processed for the inspection at the individual analyzer units.

As one of the sample racks 1 on the rack providing part 17 is moved forward to the main transfer line 20, the identification information of the sample rack 1 or the identification information of the sample container 2 is read out by the identification information read-out unit 50. The classification of the sample on the corresponding sample rack 1 is judged by the central control computer 40 with reference to the read-out information, and the group of the analyzer unit with analysis conditions defined for its corresponding sample classification is determined. Finally, according to this determination result, one of the analyzer units categorized in the selected group of the analyzer units is selected as the destination to which the sample rack or the sample container is transferred. In this embodiment, the sample to be inspected is assumed to be for serum analysis and the selected group of the analyzer unit to which the sample rack containing this sample is to be transferred is one including the analyzer units 3A, 3B and 3D.

In reading out the sample identification information, the sample number and the registration status of the analysis item are searched, and then, the designated analysis items specific to the individual samples loaded on the sample rack 1 are clarified. Finally, the central control computer 40 determines which analysis item of the designated sample should be processed by any of the analyzer units 3A, 3B or 3C. In this case, the central control computer 40 monitors the time duration until the designated number of inspection analysis operations for the designated analysis items already assigned to the individual analyzer units including the pipetting operations of the samples are completed. Specifically, as for the specific analysis items which can be processed by a plurality of analyzer units, the efficiency for the analysis operation is estimated by considering which analyzer unit should perform the specific analysis item exclusively. For example, as for the specific analysis items, GOT and GPT, determined is whether the analyzer unit 3A or 3B contains the least number of samples which are stacked on the waiting line for the inspection analysis operation, and the analyzer unit providing a shorter waiting time is assigned as the designated analyzer unit used for GOT and GPT. In this embodiment, the designated analyzer unit to be used for the inspection analysis operation for the specified analysis items is automatically selected by considering the degree of business distribution among the plurality of analyzer units. It may be allowed other than this embodiment that the analyzer unit to be used for the designated analysis items is directly specified by the inspection operator with the operation unit 42.

The sample rack 1 with its destination defined as, for example, the analyzer unit 3B, and with a designated sample to be inspected for the specified analysis item is transferred by the main transfer line 20 extended to the specified analyzer unit 3B, and stops at the entrance port to the sampling line 4B of the analyzer unit 3B. Next, the sample rack 1 is loaded onto the sampling line 4B and, and after the specified sample in the sample rack 1 located at the pipetting position is picked up and pipetted into the reaction part 5B by the sample pipetting mechanism 48b, the sample rack 1 is transferred back to the main transfer line 20. In case that there still remain samples on the sample rack 1 which contain the analysis items to be processed by another analyzer unit, the sample rack 1 is transferred to the analyzer unit 3C by the main transfer line 20, and loaded on the sampling line 4C for the pipetting operation.

The amount of the reagent fluid left in the reagent bottle used for the individual analysis items in the individual analyzer units is monitored by the central control computer 40. As for the method for monitoring the reagent fluid left in the reagent bottle, often used are a method in which the fluid level sensor attached to the reagent pipette nozzle detects the reagent fluid level in the reagent bottle when the corresponding reagent fluid is picked up and pipetted, or a method in which a pre-input maximum analyzable number is subtracted by one every pipetting of the reagent. In either of the methods described above, whether the amount of the reagent fluid used for the designated analysis items is enough or short is determined by the central control computer 4 considering whether the remaining analyzable number reaches the value or not. The lower bound value predetermined in this case is, for example, zero, 1 or 2. For example, in case that the amount of the reagent fluid for GOT stored in the specified analyzer unit 3B is proved to be short, the analysis of GOT by the analyzer unit 3B is interrupted and at the same time, the analysis of GOT is switched to the analyzer unit 3A which may contain enough of the reagent fluid for GOT inspection. Therefore, the samples to be processed for GOT inspection analysis operation are forwarded directly to the analyzer unit 3A to which the operation priority for GOT inspection is assigned thereafter.

Figure 4:
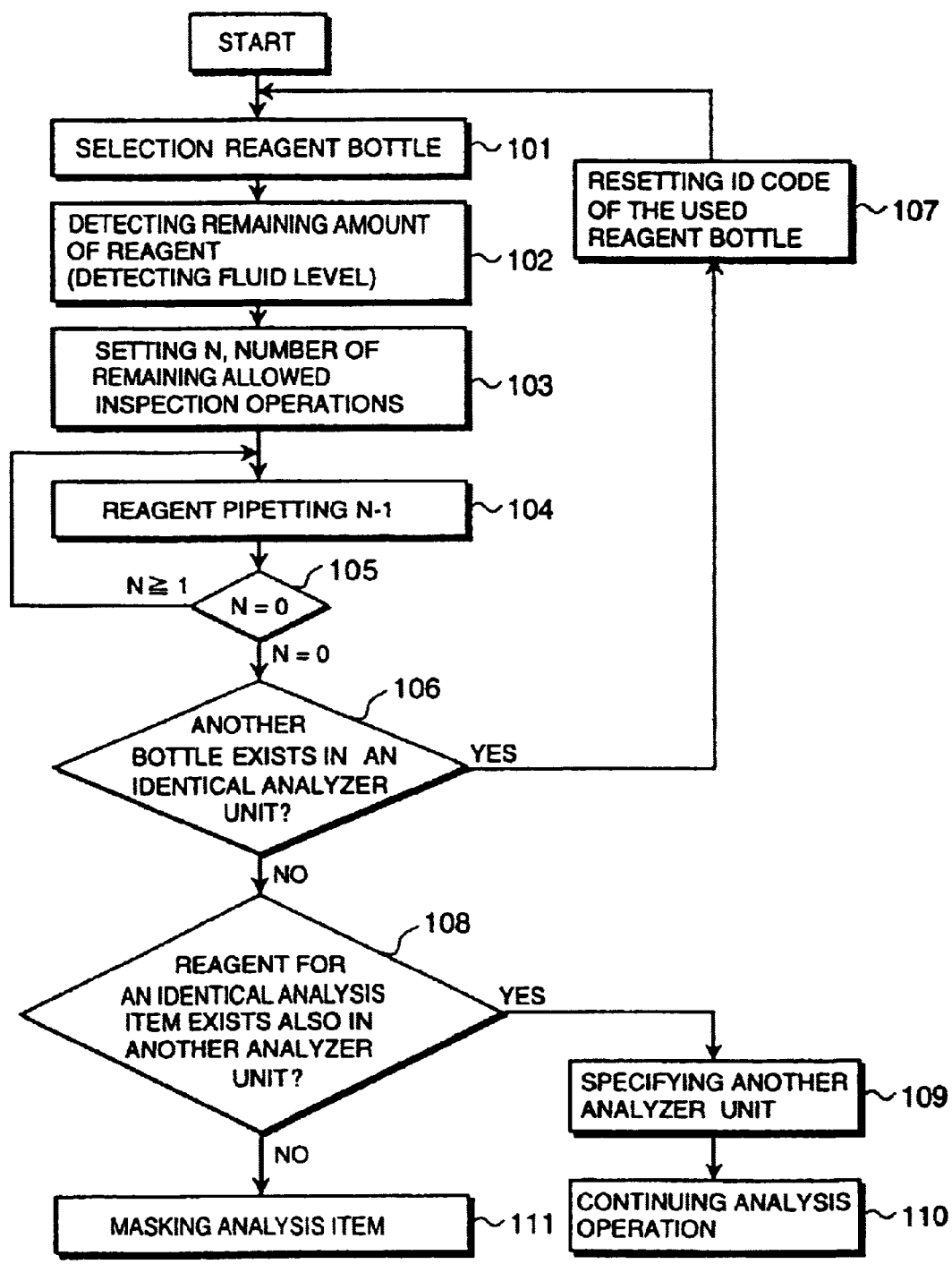
FIG. 4 is a flow chart showing a procedural flow when a reagent is found to be short.

An example of the operation flow when the amount of a reagent fluid is judged to be short will be described, referring to FIG. 4. In Step 101, in the specified analyzer unit which contains the reagent bottle used for the designated analysis item, the specified reagent bottle is selected. In Step 102, an amount of the reagent fluid left in the reagent bottle is estimated by detecting the fluid level of the reagent fluid used for the designated analysis item. In Step 103, the number of remaining tests for the designated analysis item is set in the memory unit 45. In Step 104, the number of remaining tests allowable with the consumed reagent fluid after the pipetting operation is calculated. In Step 105, the number of remaining tests is checked after every repeated pipetting operation of the reagent fluid. If the remaining number of available tests is zero, the processing proceeds to Step 106, but if the remaining number of available tests is not smaller than 1, the processing returns to Step 104.

In Step 106, it is judged whether another reagent bottle for the same kind of analysis item is loaded on the reagent delivery mechanism in an identical analyzer unit or not. If another reagent bottle is loaded, the processing proceeds to Step 107 to reset the identification code of the reagent bottle which has been used, and then the processing returns to Step 101 to select another new reagent bottle for the same kind of analysis item. If another reagent bottle is not loaded, the processing proceeds to Step 108 to judge whether another reagent bottle for the same kind of analysis item is loaded on another analyzer unit or not. If the designated reagent bottle is found on another analyzer unit in Step 108, the processing proceeds to Step 109, where the central control computer dispatches this analyzer unit for the subsequent analysis for the samples with respect to the designated analysis item. At the same time, the central control computer disables the inspection analysis function for the designated analysis item on the specified analyzer unit previously used for the designated analysis item. With the above described control operations, the sample with analysis items predefined which is not processed on the current analyzer unit is transferred through the rack providing portion 17 to the other analyzer unit, and in Step 110, the subsequent analysis operations for this sample are continued in the other analyzer unit. If the designated reagent bottle is not found on the other analyzer unit in Step 108, the processing proceeds to Step 111 to perform masking so as to stop analysis for the designated analysis item on the overall analyzer system.

The control unit of the embodiment shown in FIG. 1 manages the status of dispatching the inspection analysis operations for the individual analysis item onto the specified analyzer unit, and this status information is stored in the memory unit 45. The information in regard to which analysis item is processed by which analyzer unit is stored on the memory table in the central control computer 40, and this information is displayed in a table format on a CRT 43 or output from a printer 44 according to a request of the operator.

In the unit of the embodiment shown in FIG. 1, the startup and shutdown operation of the individual analyzer unit 3A to 3G can be specified by the key installed in the operation unit 42. Based on the key-oriented specification information supplied by the operation unit 42, the central control computer 40 makes the sample move from the rack providing portion 17 and transferred through the transfer line 20 to the currently operable analyzer unit other than the analyzer unit currently shutdown. Especially at the night shift work when the number of samples requesting to be analyzed is relatively small and the emergency inspection analysis are mainly operated, it may be allowed to operate, for example, only the analyzer unit 3C exclusive for the samples for the blood serum inspection analysis and the analyzer unit 3G exclusive for the samples for the urine inspection analysis. When the number of samples requesting to be analyzed increases, a plurality of analyzer units currently shutdown are started up.

In the unit of the embodiment shown in FIG. 1, in case that the analysis operation by the designated analyzer unit is disabled when any fault occurs in any of the analyzer units the control unit manages to load the sample rack onto another operable analyzer unit and controls the analysis operation by the operable analyzer unit. For example, by installing plural reagent fluids in the two analyzer units 3B and 3C redundantly, the analysis operations for plural analysis items can be performed continuously.

According to the present invention, as the reagent fluid for the same kind of analysis item is installed in plural analyzer units including the designated analyzer unit and another one, the specified analysis item can be inspected by any of the plural analyzer units, and as the sample with the specified analysis item can be dynamically dispatched onto the adequate analyzer unit even if a large number of samples are assigned to the designated single analyzer unit, the analysis item requested by a large number of samples can be efficiently to processed the time for the analysis operation can be globally reduced. Furthermore, as the status of the shortage of the reagent fluid for the designated analysis item in the specified analyzer unit is judged and the sample with the designated analysis item is transferred to another analyzer unit where the designated analysis item is inspected, the state that the analysis operation is interrupted due to the shortage of the reagent fluid can be avoided.

What is claimed is:

1. A multiple sample analyzing system, comprising:

a transfer line;

a plurality of analyzer units arranged along the transfer line, the transfer line transferring a sample rack holding a plurality of samples to the analyzer units for analysis thereby, wherein the same reagent used for one specific analysis is included in those analyzer units that perform that specific analysis;

means for reading out identification information of the sample rack transferred by the transfer line;

a controller for judging which analyzer unit to send the sample rack on the basis of the read-out identification information;

instruction means for instructing a start-up operation and a shutdown operation of each analyzer unit;

means for communicating instruction information regarding the start-up status or shutdown status of each analyzer unit to said controller;

wherein the controller controls the transfer line to transfer the sample rack to an analyzer unit other than an analyzer unit whose operation is shut down on the basis of the judgement of the controller from the read-out identification information and the start-up or shutdown status instruction information from the instruction means.

2. A multiple sample analyzing system according to claim 1, wherein the specific analysis is a liver function inspection analysis item or an emergency analysis item.

* * * * *